United States Patent [19]

Umemura et al.

[11] 4,171,328
[45] Oct. 16, 1979

[54] CATALYTIC OXIDATION OF ISOBUTYLENE

[75] Inventors: Sumio Umemura; Kyoji Ohdan; Kenichi Suzuki; Terumi Hisayuki, all of Ube, Japan

[73] Assignee: Ube Industries Ltd., Yamaguchi, Japan

[21] Appl. No.: 917,793

[22] Filed: Jun. 22, 1978

[30] Foreign Application Priority Data

Nov. 7, 1977 [JP] Japan ................................ 52-132440

[51] Int. Cl.² ............................................. C07C 45/02
[52] U.S. Cl. .................................................. 260/604 R
[58] Field of Search ..................................... 260/604 R

[56] References Cited

U.S. PATENT DOCUMENTS

| 3,236,787 | 12/1966 | Koch | 252/411 |
|---|---|---|---|
| 3,600,443 | 8/1971 | Ceuidalli et al. | 260/604 R |
| 4,065,507 | 12/1977 | Hardman | 260/604 R |

FOREIGN PATENT DOCUMENTS

| 48-1645 | of 1973 | Japan | 260/604 R |
|---|---|---|---|
| 48-52713 | of 1973 | Japan | 260/604 R |
| 51-12604 | of 1976 | Japan | 260/604 R |
| 51-34107 | of 1976 | Japan | 260/604 R |
| 51-93793 | of 1976 | Japan | 260/604 R |
| 1351646 | 5/1974 | United Kingdom | 260/604 R |

Primary Examiner—Werren B. Lone
Attorney, Agent, or Firm—Burgess, Ryan and Wayne

[57] ABSTRACT

Isobutylene is catalytically oxidized in the vapor phase with molecular oxygen to form methacrolein. The catalyst used consists essentially of metal oxides and is represented by the formula:

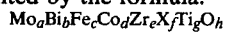

$Mo_aBi_bFe_cCo_dZr_eX_fTi_gO_h$ wherein Mo=molybdenum, Bi=bismuth, Fe=iron, Co=cobalt, Zr=zirconium, X=calcium and/or zinc, Ti=titanium and O=oxygen, and the subscripts indicating the atomic ratios of the respective metals to bismuth are: a=5–20, b=1, c=0.2–5, d=1–10, e=0.01–2, f=0.01–2, and g=0.01–1. The catalyst exhibits little or no reduction in mechanical strength during the oxidation reaction and results in an enhanced yield of methacrolein.

11 Claims, No Drawings

CATALYTIC OXIDATION OF ISOBUTYLENE

This invention relates to a process for catalytically oxidizing isobutylene in the vapor phase with molecular oxygen to form methacrolein, wherein an improved catalyst having enhanced mechanical strength which provides enhanced yield of methacrolein is used.

Many proposals have been heretofore made to catalytically oxidize α-olefins such as propylene and isobutylene in the vapor phase with molecular oxygen to form olefinically unsaturated aldehydes such as acrolein and methacrolein. It is generally accepted that most catalysts heretofore proposed exhibit reduced catalytic activity for the oxidation of isobutylene into methacrolein as compared with the catalytic activity for the oxidation of propylene into acrolein. In fact, the inventors have found that the yield of methacrolein from isobutylene is generally lower than the yield of acrolein from propylene, provided that the same catalyst is used in the respective oxidation reactions. It is presumed that one of the reasons for which the yield of methacrolein is lower than that of acrolein is that isobutylene is composed of a branched carbon chain. It is, therefore, eagerly desired to develop a catalyst exhibiting enhanced catalytic activity for the oxidation of isobutylene into methacrolein.

Typical catalysts heretofore proposed for use in the oxidation of isobutylene into methacrolein are based on the four metal ingredients, i.e., molybdenum, bismuth, iron and cobalt. For example, catalysts having the following compositions are known: Mo-Bi-Fe-Co-Ni-Tl-O (British Pat. No. 1,351,646), Co-Fe-Bi-Cr-K-Mo-O (Japanese Patent Publication No. 1,645/1973), Co-Fe-W-Bi-Mo-Si-Tl-O (Japanese Patent Publication No. 12,604/1976), Mn-K-Co-Ni-Fe-Bi-Mo-O (Japanese Patent Laid-open Application No. 34,107/1976), Mo-Bi-Fe-Co-Zr-O (Japanese Patent Laid-open Application No. 93,793/1976) and Co-Fe-Bi-K-Mo-O (Japanese Patent Laid-open Application No. 52,713/1973). The catalysts containing the four metal ingredients, i.e., molybdenum, bismuth, iron and cobalt, which include the above-listed known catalysts, generally exhibit relatively enhanced selectivity to and yield of methacrolein as compared with other catalysts which do not contain one or more of the four metal ingredients.

However, the above-mentioned catalysts containing molybdenum, bismuth, iron and cobalt ingredients are not advantageous in that molybdenum contained therein is liable to be lost from the catalysts during the reaction, and the loss leads to reduction in the catalytic activity and reduction in the mechanical strength of the catalyst, and, consequently, shortening of the catalyst life. Such undesirable molybdenum loss becomes conspicuous with an increase of the reaction temperature.

An object of the present invention is to improve conventional catalysts based mainly on molybdenum, bismuth, iron and cobalt and a process carried out therewith for the oxidation of isobutylene in the vapor phase to methacrolein. A further object of the invention is to particularly provide a catalyst which is capable of giving enhanced conversion of isobutylene and selectivity to methacrolein and thus an enhanced yield of methacrolein even when the oxidation reaction is conducted at a relatively low temperature and for a relatively short contact time, and which is further capable of exhibiting a long catalyst life.

Other objects and advantages of the present invention will be apparent from the following description.

In accordance with the present invention, there is provided a process for catalytically oxidizing isobutylene at an elevated temperature in the vapor phase with molecular oxygen to form methacrolein, which comprises passing a gaseous feed comprising isobutylene and molecular oxygen over a catalyst consisting essentially of metal oxides represented by the formula:

$$Mo_aBi_bFe_cCo_dZr_eX_fTi_gO_h$$

wherein Mo is molybdenum, Bi is bismuth, Fe is iron, Co is cobalt, Zr is zirconium, X is at least one metal selected from calcium and zinc, Ti is titanium and O is oxygen, and each of the subscripts a through g is a positive number indicating an atomic ratio of the respective metal to bismuth and falling within the following ranges: a=5 to 20, preferably 7 to 15, b=1, c=0.2 to 5, preferably 0.5 to 4, d=1 to 10, preferably 2 to 9, e=0.01 to 2, preferably 0.05 to 1.5, f=0.01 to 2, preferably 0.05 to 1.5, and g=0.01 to 1, preferably 0.02 to 0.8, and h is a positive number satisfying the average valency of the respective metals.

The atomic ratios of the respective metal ingredients to bismuth, expressed by the subscripts in the above-mentioned formula are crucial for the intended advantages. If one or more of the atomic ratios of molybdenum, iron and cobalt to bismuth, i.e., subscripts (a), (c) and (d), are outside the above-mentioned ranges, both the conversion of isobutylene and the selectivity to methacrolein are reduced. If one or more of the atomic ratios of zirconium, titanium and calcium and/or zinc to bismuth, i.e., (e), (g) and (f), are lower than the above-mentioned ranges, the catalyst is liable to be reduced in terms of mechanical strength during the oxidation reaction. In contrast, if one or more of the atomic ratios of these metals to bismuth are higher than the above-mentioned ranges, the conversion of isobutylene and/or the selectivity to methacrolein is liable to be reduced. Furthermore, if one or more of zirconium, titanium and calcium and/or zinc are omitted, (1) the binding strength of the catalyst is insufficient for withstanding the external force applied thereto during the preparation thereof, (2) the strength of the catalyst tends to be reduced during the oxidation reaction, and (3) the yield of methacrolein is decreased.

The respective metal ingredients are present in the form of metal oxides in the catalyst, which oxides include those of the type in which a single metal is bonded with oxygen, those of the type in which two or more metals are bonded with oxygen, and a combination of both types of above-mentioned oxides.

The catalyst used in the process of the invention may be prepared in any convenient manner by using, as the starting raw material, oxides, salts and other compounds, containing the above-mentioned metal ingredients. However, calcination of the catalyst, i.e., the final step of the catalyst preparation, should preferably be carried out at a temperature in the range of from 600° to 800° C., more preferably 650° to 750° C., and over a period of 2 to 10 hours, for the desired yield of methacrolein and catalyst strength. This temperature range is higher than those popularly employed for conventional catalysts based on molybdenum, bismuth, iron and cobalt.

The general procedure for the preparation of the catalyst is as follows. Oxides, salts and other compounds, containing the above-mentioned metal ingredients are mixed with each other in an aqueous medium to prepare a uniform dispersion. The aqueous dispersion is heated at a temperature of from 100° to 150° C., preferably approximately 120° C., to evaporate water, and then, heated at a temperature of from 150° to 300° C., preferably approximately 200° C., for a period of 3 to 20 hours to eliminate nitrogen-containing compounds such as ammonium nitrate and nitrogen oxides. The dried product is shaped into pellets or particulates of desired shape and size. The shaped pellets or particulates are calcined under the above-mentioned conditions.

The procedure for the preparation of the catalyst will be described in more detail with reference to a catalyst consisting of molybdenum, bismuth, iron, cobalt, calcium, zirconium, titanium and oxygen.

Predetermined amounts of ammonium molybdate and titanium dioxide are dissolved or suspended in warm water. Added by drops to this aqueous suspension, while the mixture being stirred, are a solution of a predetermined amount of bismuth nitrate in nitric acid and a solution in warm water of predetermined amounts of zirconium nitrate, iron nitrate, cobalt nitrate and calcium nitrate. The so obtained aqueous slurry was heated at a temperature of approximately 120° C. and then, again heated at a temperature of approximately 200° C., for a period of from 3 to 20 hours, to dry the aqueous slurry. The dried product is finally calcined at a temperature of from 600° to 800° C., preferably from 650° to 750° C., for a period of from 1 to 20 hours, preferably from 2 to 10 hours.

As illustrations of the starting raw materials for use in the preparation of the catalyst are enumerated, for example, molybdenum compounds such as molybdic acid, ammonium molybdate and molybdenum trioxide; cobalt compounds such as cobalt carbonate, cobalt nitrate, cobaltous oxide, tricobalt tetraoxide, cobalt chloride, cobaltous hydroxide, cobaltic hydroxide and cobalt sulfide; iron compounds such as ferrous nitrate, ferric nitrate, ferrous oxide, ferric oxide, ferrous carbonate, ferrous sulfide, ferrous chloride, ferric chloride, ferrous hydroxide, ferric hydroxide, ferrous sulfate, ferric sulfate, ammonium ferrous sulfate and ammonium ferric sulfate; bismuth compounds such as bismuth nitrate, bismuth dichloride, bismuth trichloride, bismuth pentoxide, bismuth trioxide, bismuth tetroxide, bismuth oxynitrate, bismuth hydroxide, bismuth subnitrate and bismuth oxychloride; zirconium compounds such as zirconium nitrate, zirconium oxide, zirconium chloride, zirconyl nitrate, zirconium hydroxide and zirconium sulfate; calcium compounds such as calcium nitrate, calcium chloride, calcium carbonate and calcium hydroxide; zinc compounds such as zinc nitrate, zinc hydroxide, zinc chloride and zinc carbonate; and titanium compounds such as titanium oxide and titanic acid. Among these compounds, those which are capable of being readily soluble in water, an acid such as nitric acid or an alkaline solution such as aqueous ammonia are preferable because a completely uniform mixture is readily obtainable.

The catalyst may be used alone or in combination with a carrier. As carriers, those which are known for use supporting conventional oxidation catalysts and bring favorable effects for the reaction involved, such as silica, alumina, silica-alumina, titania, diatomaceous earth and carborundum may be used. These carriers may be combined with the catalyst either during or after the preparation of the catalyst.

In general, the size and shape of the catalyst particulate used, and the use of a carrier are not critical because they do not greatly affect the catalytic activity.

A gaseous feed comprising isobutylene and molecular oxygen may contain a diluent gas which does not influence the oxidation reaction. Such a diluent gas includes, for example, steam, nitrogen and carbon dioxide. Steam present in the gaseous feed not only acts as a diluent but also exhibits effects to enhance the selectivity to methacrolein and to make the catalytic activity durable. Accordingly, it is generally preferred to incorporate steam into the gaseous feed. The amount of steam incorporated is preferably in the range of from 0.1 to 8 moles, more preferably from 1 to 5 moles, per mole of isobutylene.

The isobutylene used is not necessarily highly purified, but the isobutylene may contain a minor amount of other hydrocarbons such as n-butane and n-butene. The amount of such hydrocarbons should be less than 0.5 mole, preferably less than 0.1 mole, per mole of isobutylene.

Likewise, molecular oxygen used is also not necessarily highly purified, but oxygen-containing gases such as air, and mixture of molecular oxygen and the above-mentioned diluent gas, may conveniently be used. Particularly, air may be advantageously used. The relative proportion of molecular oxygen in the gaseous feed is usually in the range of from 0.8 to 4 moles, more preferably from 1 to 2.5 moles, per mole of isobutylene.

The catalytic oxidation reaction of the present invention may be carried out at a temperature in the range of from 250° to 500° C., preferably 300° to 450° C. The contact time is usually in the range of from 0.3 to 20 seconds, preferably from 0.5 to 15 seconds. Optimum results are obtained at the reaction temperature of approximately 330° C. and the contact time of approximately 3 seconds. The reaction may be carried out under atmospheric pressure although slightly superatmospheric or subatmospheric pressure may be used if desired.

The catalytic oxidation reaction may be carried out in a fixed bed, a moving bed or a fluidized bed. When a fluidized bed is employed, it is preferable to use a catalyst having a particle size in the range of from 30 to 100 microns. Furthermore, even if steam is not incorporated into the gaseous feed, the hereinbefore-mentioned favorable effects can be obtained in the fluidized bed reaction. This is because water produced by the reaction has a similar effect.

The catalyst used in the process of the present invention results, even when the oxidation reaction is carried out at a relatively low temperature, e.g. approximately 330° C., and a relatively short contact time, e.g. approximately 3 seconds, in satisfactory conversion of isobutylene and selectivity to methacrolein, and a high yield of methacrolein exceeding 80%. Furthermore, the mechanical strength of the catalyst is reduced only to a slight extent during the catalytic oxidation reaction. Thus, the process of the present invention is advantageous from a commercial standpoint.

The present invention will be further clarified by the following examples and comparative examples, wherein "%" is expressed by weight unless otherwise specified. In these examples, the conversion of isobutylene, yield of methacrolein and selectivity to methacrolein were calculated in accordance with the following equations.

% conversion of isobutylene =

$$\frac{\text{moles of isobutylene consumed}}{\text{moles of isobutylene fed}} \times 100$$

% selectivity to methacrolein =

$$\frac{\text{moles of methacrolein produced}}{\text{moles of isobutylene consumed}} \times 100$$

% yield of methacrolein =

$$\frac{\text{moles of methacrolein produced}}{\text{moles of isobutylene fed}} \times 100$$

The moles of isobutylene fed, the moles of isobutylene consumed and the moles of methacrolein produced were determined after one hour had elapsed from the commencement of the reaction.

The crush strength of the catalyst was determined as follows.

10 ml of a catalyst specimen (approximately 50 tablets, each being 5 mm in diameter and 5 mm in height) were packed into a tubular glass reactor tube having an inner diameter of 20 mm. A gaseous mixture of isobutylene, steam and air, the molar ratio of the three components being 10:40:100, respectively, was passed through the catalyst-packed reactor maintained at 380° C. at a flow rate of 150 ml/min over a period of 100 hours. The crush strength of each of the approximately 50 tablets was measured by using a Kiya-type durometer, and the average crush strength was calculated therefrom and expressed in Kg. The crush strength was measured before and after the above-mentioned reaction for comparison purposes.

EXAMPLE 1

343.6 g of ammonium molybdate [$(NH_4)_6Mo_7O_{24}.4H_2O$] were dissolved in 450 ml of water maintained at 80° C. 3.1 g of titanium dioxide [$TiO_2$] were added to the aqueous ammonium molybdate solution, while the mixture was being stirred. Added by drops to the so obtained slurry during stirring of the mixture were both a solution of 94.4 g of bismuth nitrate [$Bi(NO_3)_3.5H_2O$] in 110 ml of a 15% nitric acid and a solution of 266.6 g of cobaltous nitrate [$Co(NO_3)_2.6H_2O$], 148.0 g of ferric nitrate [$Fe(NO_3)_3.9H_2O$], 4.6 g of zirconyl nitrate [$ZrO(NO_3)_2.2H_2O$] and 4.6 g of calcium nitrate [$Ca(NO_3)_2.4H_2O$] in 150 ml of warm water maintained at 80° C. Thereafter, the slurry so obtained was spray-dried at 120° C. and then further dried at 200° C. for five hours to obtain a dry powder. The dry powder was shaped into tablets 5 mm in diameter and 5 mm in height by using a tableting machine. The tablets were calcined at 670° C. for 10 hours in air to prepare a catalyst. The atomic ratio of the metal ingredients contained in the catalyst was Mo:Bi:Fe:Co:Zr:Ca:Ti = 10:1:2:8:0.1:0.1:0.2.

Eight ml of the catalyst were packed into a U-shaped tubular glass reactor having an inner diameter of 8 mm. A gaseous mixture of isobutylene, air and steam, the molar ratio of the three ingredients being 10:100:40, respectively, was passed through the catalyst-packed reactor maintained at 330° C. at a flow rate of 150 ml/min. The contact time was 3.2 seconds.

The conversion of isobutylene, the selectivity to methacrolein and the yield of methacrolein were 94.7%, 85.3% and 80.8%, respectively. The crush strength of the catalyst was 7.8 kg before the reaction and 7.6 kg after the reaction.

EXAMPLES 2 through 8

By following a procedure similar to that mentioned in Example 1, catalysts containing the seven metal ingredients (Mo, Bi, Fe, Co, Zr, Ca and Ti) at varied atomic ratios as shown in Table I, below, were prepared. Using these catalysts separately, the vapor phase oxidation of isobutylene was carried out under conditions similar to those mentioned in Example 1. Results are shown in Table I, below.

EXAMPLES 9 and 10

By following a procedure similar to that mentioned in Example 1, two catalysts were prepared. In the preparation of one of the catalysts, zinc nitrate [$Zn(NO_3)_2.6H_2O$] was used instead of calcium nitrate [$Ca(NO_3)_2.4H_2O$]. In the preparation of the other catalyst, both zinc nitrate [$Zn(NO_3)_2.6H_2O$] and calcium nitrate [$Ca(NO_3)_2.4H_2O$] were used instead of the calcium nitrate alone. The two catalysts contained the respective metal ingredients at the atomic ratios shown in Table I, below.

Using these catalysts separately, the vapor phase oxidation of isobutylene was carried out under conditions similar to those mentioned in Example 1. Results are shown in Table I, below.

COMPARATIVE EXAMPLES 1 through 4

By following a procedure similar to that mentioned in Example 1, four catalysts were prepared wherein a part of the seven metal compounds was not used with all other conditions remaining substantially the same. These four catalysts contained the respective metal ingredients at the atomic ratios shown in Table I, below.

Table I

| Example No. | Catalyst (atomic ratio) | | | | | | | | Conversion of isobutylene (%) | Selectivity to methacrolein (%) | Yield of methacrolein (%) | Crush strength of catalyst (kg) | |
|---|---|---|---|---|---|---|---|---|---|---|---|---|---|
| | Mo | Bi | Fe | Co | Zr | Ca | Zn | Ti | | | | Before reaction | After reaction |
| Example | | | | | | | | | | | | | |
| 2 | 7 | 1 | 1 | 8 | 0.1 | 0.1 | — | 0.2 | 96.1 | 86.6 | 83.2 | 7.9 | 7.7 |
| 3 | 13 | 1 | 2 | 8 | 0.2 | 0.1 | — | 0.1 | 97.4 | 84.6 | 82.4 | 6.9 | 6.6 |
| 4 | 10 | 1 | 1 | 8 | 0.1 | 0.1 | — | 0.2 | 97.6 | 85.7 | 83.6 | 7.0 | 6.9 |
| 5 | 10 | 1 | 2 | 8 | 0.2 | 0.1 | — | 0.05 | 94.4 | 85.0 | 80.2 | 8.1 | 7.9 |
| 6 | 10 | 1 | 2 | 7 | 0.1 | 0.5 | — | 0.2 | 95.2 | 85.1 | 81.0 | 8.8 | 8.6 |
| 7 | 10 | 1 | 2 | 9 | 0.1 | 0.1 | — | 1 | 94.9 | 86.3 | 81.9 | 10.7 | 10.4 |
| 8 | 10 | 1 | 2 | 8 | 0.2 | 0.1 | — | 0.2 | 96.4 | 84.1 | 81.1 | 7.6 | 7.4 |
| 9 | 10 | 1 | 2 | 8 | 0.2 | — | 0.2 | 0.2 | 95.9 | 84.0 | 80.6 | 7.2 | 6.9 |
| 10 | 10 | 1 | 2 | 8 | 0.2 | 0.1 | 0.2 | 0.2 | 96.1 | 84.8 | 81.5 | 7.5 | 7.3 |
| Comparative | | | | | | | | | | | | | |

Table I-continued

| Example No. | Catalyst (atomic ratio) | | | | | | | | Conversion of isobutylene (%) | Selectivity to methacrolein (%) | Yield of methacrolein (%) | Crush strength of catalyst (kg) | |
|---|---|---|---|---|---|---|---|---|---|---|---|---|---|
| | Mo | Bi | Fe | Co | Zr | Ca | Zn | Ti | | | | Before reaction | After reaction |
| Example 1 | 10 | 1 | 1 | 8 | — | — | — | — | 100 | 79.5 | 79.5 | 4.4 | 3.0 |
| 2 | 10 | 1 | 2 | 7 | 0.1 | — | — | — | 94.5 | 82.0 | 77.5 | 5.2 | 3.4 |
| 3 | 10 | 1 | 1 | 8 | 0.1 | 0.1 | — | — | 93.3 | 81.4 | 75.9 | 4.6 | 3.3 |
| 4 | 10 | 1 | 2 | 8 | — | 0.1 | — | 0.2 | 91.9 | 80.3 | 73.8 | 5.8 | 4.6 |

(Reaction temperature = 330° C., contact time = 3.2 seconds)

COMPARATIVE EXAMPLE 5

70.0 g of cobaltous nitrate [Co(NO$_3$)$_2$.6H$_2$O] and 24.3 g of ferric nitrate [Fe(NO$_3$)$_3$.5H$_2$O] were dissolved in 40 ml of warm water maintained at 80° C. 29.0 g of bismuth nitrate [Bi(NO$_3$)$_3$.5H$_2$O] were dissolved in 30 ml of water acidified with 6 ml of concentrated nitric acid. The two solutions so obtained were combined with each other. The combined solution was added by drops, while being stirred, to a solution of 106.2 g of ammonium molybdate [(NH$_4$)$_6$.Mo$_7$O$_{24}$.4H$_2$O] and 32.4 g of ammonium paratungstate [(NH$_4$)$_{10}$.W$_{12}$O$_{41}$.5H$_2$O] in 300 ml of warm water. Added to the solution so obtained, were first a solution of 0.801 g of thallium nitrate [TlNO$_3$] in 10 ml of water and then 24.4 g of a 20% silica sol. The resultant mixture was, while being heated and stirred, evaporated to dryness to obtain a solid agglomerate. The agglomerate was pulverized and then shaped into tablets 5 mm in diameter and 5 mm in height by using a tableting machine. The tablets were calcined at 450° C. for 6 hours in air to prepare a catalyst. The atomic ratio of the metal ingredients contained in the catalyst was Mo:Bi:Fe:Co:W:Tl=10:1:1:4:2:0.05.

The catalyst exhibited a crush strength of 6.3 kg before the reaction and a crush strength of 4.5 kg after the reaction.

What we claim is:

1. In a process for catalytically oxidizing isobutylene at a temperature in the range of from 250° to 500° in the vapor phase with molecular oxygen to form methacrolein, the improvement which comprises passing a gaseous feed comprising isobutylene and molecular oxygen in a catalytic oxidation reaction zone over a catalyst consisting essentially of metal oxides represented by the formula:

$$Mo_aBi_bFe_cCo_dZr_eX_fTi_gO_h$$

wherein Mo is molybdenum, Bi is bismuth, Fe is iron, Co is cobalt, Zr is zirconium, X is at least one metal selected from the group consisting of calcium and zinc, Ti is titanium and O is oxygen, and each of the subscripts a through g is a positive number indicating an atomic ratio of the respective metal to bismuth and falling within the following ranges: a=5 to 20, b=1, c=0.2 to 5, d=1 to 10, e=0.01 to 2, f=0.01 to 2 and g=0.01 to 1, and h is a positive number satisfying the average valency of the respective metals.

2. A process according to claim 1 wherein the atomic ratios of the respective metals to bismuth are such that the subscripts a through g fall within the following ranges: a=7 to 15, b=1, c=0.5 to 4, d=2 to 9, e=0.05 to 1.5, f=0.05 to 1.5 and g=0.02 to 0.8.

3. A process according to claim 1 wherein X in the formula is calcium.

4. A process according to claim 1 wherein X in the formula is zinc.

5. A process according to claim 1 wherein the contact time in the catalytic oxidation reaction zone is in the range of from 0.3 to 20 seconds.

6. A process according to claim 1 wherein the reaction temperature is in the range of from 300° to 450° C.

7. A process according to claim 1 wherein the relative proportion of molecular oxygen to isobutylene in the gaseous feed is in the range of from 0.8 to 4 moles per mole of isobutylene.

8. A process according to claim 1 wherein the gaseous feed further contains 0.1 to 8 moles of steam per mole of isobutylene.

9. A process according to claim 1 wherein said catalyst metal oxides are the calcined residue of a product formed by mixing in an aqueous medium the respective metal-containing compounds and then drying the mixture; said metal-containing compounds being in the form of an oxide, salt or a mixture thereof.

10. A process according to claim 9 wherein said calcined residue is obtained by calcining said mixed and dried product at a temperature in the range of from 600° to 800° C.

11. A process according to claim 9 wherein said drying of the mixture is carried out in two stages, in the first stage of which the mixture is maintained at a temperature of from 100° to 150° C. and in the second stage of which the mixture is maintained at a temperature of from 150° to 300° C.

* * * * *